US010610417B2

(12) United States Patent
Wada (10) Patent No.: US 10,610,417 B2
(45) Date of Patent: Apr. 7, 2020

(54) COMPOSITE SHEET MANUFACTURING DEVICE AND COMPOSITE SHEET MANUFACTURING METHOD

(71) Applicant: ZUIKO CORPORATION, Osaka (JP)

(72) Inventor: Takao Wada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 912 days.

(21) Appl. No.: 15/028,958

(22) PCT Filed: Oct. 10, 2014

(86) PCT No.: PCT/JP2014/077167
§ 371 (c)(1),
(2) Date: Apr. 13, 2016

(87) PCT Pub. No.: WO2015/060141
PCT Pub. Date: Apr. 30, 2015

(65) Prior Publication Data
US 2016/0250079 A1 Sep. 1, 2016

(30) Foreign Application Priority Data

Oct. 22, 2013 (JP) .................................. 2013-218947
Oct. 22, 2013 (JP) .................................. 2013-218948

(51) Int. Cl.
*B26D 1/00* (2006.01)
*A61F 13/15* (2006.01)
(Continued)

(52) U.S. Cl.
CPC ........ *A61F 13/15723* (2013.01); *B26D 1/365* (2013.01); *B26D 1/405* (2013.01);
(Continued)

(58) Field of Classification Search
CPC .......... B26D 1/365; B26D 1/35; B26D 5/007; B26D 7/2628; B26D 7/265
See application file for complete search history.

(56) References Cited

U.S. PATENT DOCUMENTS 5,058,496 A * 10/1991 Wittkopf ............... B21B 31/076
100/155 R
5,388,490 A * 2/1995 Buck .................... B26D 7/2628
83/344

(Continued)

FOREIGN PATENT DOCUMENTS

| CA | 2409024 A1 | 11/2002 |
| CN | 101205663 A | 6/2005 |

(Continued)

OTHER PUBLICATIONS

International Search Report.
(Continued)

*Primary Examiner* — Chelsea E Stinson
(74) *Attorney, Agent, or Firm* — Gerald E. Hespos; Michael J. Porco; Matthew T. Hespos (57) ABSTRACT

It is aimed to provide a composite sheet manufacturing device and a composite sheet manufacturing method capable of maintaining high cutting performance of a cutter by suppressing the adhesion of an adhesive of an adhesive surface to the cutter. A first sheet (42) introduced to between a cutter roller (2) and an anvil roller (3) is cut into strips (42*a*) while these rollers (2, 3) are rotated relative to each other, adhesive surfaces (*a*) of the strips (42*a*) are adhered onto a second sheet (43) for compounding, and at least one of a cutter (12) of the cutter roller (2) and the anvil roller (3) is cooled by a refrigerant by a cooling unit (20, 21).

4 Claims, 7 Drawing Sheets

(51) Int. Cl.
  *B65H 35/08* (2006.01)
  *B65H 39/14* (2006.01)
  *B26D 1/40* (2006.01)
  *B26D 1/36* (2006.01)
  *B26D 7/10* (2006.01)
  *B26D 7/08* (2006.01)

(52) U.S. Cl.
  CPC ............... *B26D 7/08* (2013.01); *B26D 7/10* (2013.01); *B65H 35/08* (2013.01); *B65H 39/14* (2013.01); *B65H 2301/5305* (2013.01); *B65H 2404/1361* (2013.01); *B65H 2406/4212* (2013.01); *B65H 2801/57* (2013.01)

(56) References Cited

U.S. PATENT DOCUMENTS

| | | | |
|---|---|---|---|
| 2007/0074809 A1 | 4/2007 | Phillips | |
| 2011/0132522 A1* | 6/2011 | Green | B26D 7/10 156/80 |
| 2013/0042771 A1 | 2/2013 | Alkhagen | |
| 2014/0225308 A1 | 8/2014 | Okuda et al. | |

FOREIGN PATENT DOCUMENTS

| | | |
|---|---|---|
| CN | 101205663 A | 6/2008 |
| CN | 102792475 A | 11/2012 |
| EP | 2641582 A1 | 9/2013 |
| JP | 52-60486 | 5/1977 |
| JP | 2001-38675 | 2/2001 |
| JP | 2007-153382 | 6/2007 |
| JP | 2007-259952 | 10/2007 |
| JP | 2012-214921 | 11/2012 |
| WO | 0188452 A1 | 11/2001 |

OTHER PUBLICATIONS

Extended European Search Report dated May 15, 2017.
Chinese Office Action dated May 27, 2016 for Application No. 201320685549.X.
Chinese Office Action dated May 27, 2016.

* cited by examiner

COMPOSITE SHEET MANUFACTURING DEVICE AND COMPOSITE SHEET MANUFACTURING METHOD

TECHNICAL FIELD

The present invention relates to a composite sheet manufacturing device and a composite sheet manufacturing method.

BACKGROUND ART

Figure 7A:
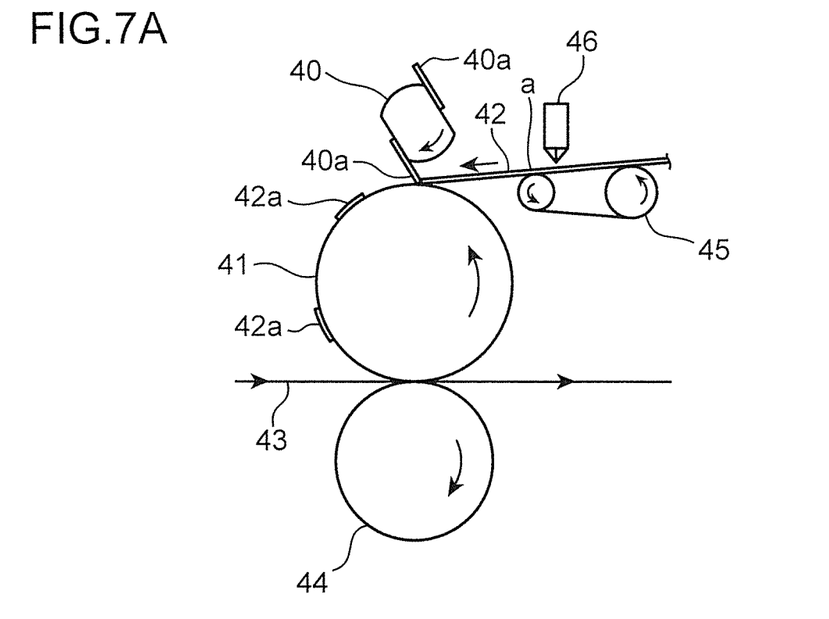
FIG. 7A is a front view of a conventional composite sheet manufacturing device.

Conventionally, a composite sheet manufacturing device cuts a first sheet 42 passed through between a cutter roller 40 and an anvil roller 41 into strips 42a by a cutter 40a of the cutter roller 40 while rotating the cutter roller 40 and the anvil roller 41 relative to each other as shown in FIG. 7A. Then, an adhesive surface a of the strip 42a having an adhesive applied thereto is adhered onto a second sheet 43 for compounding (see Japanese Unexamined Patent Publication No. 2007-259952).

Further, the composite sheet manufacturing device is provided with a press roller 44 for pressing the strips 42a adhered onto the second sheet 43 against the outer peripheral surface of the anvil roller 41 via the second sheet 43. This press roller 44 firmly adheres the adhesive surfaces a of the strips 42a to the second sheet 43.

Furthermore, the composite sheet manufacturing device is provided with a carrying conveyor 45 for conveying the first sheet 42 to between the both rollers 40 and 41 and a coating unit 46 for coating the adhesive to the first sheet 42.

Figure 7B:
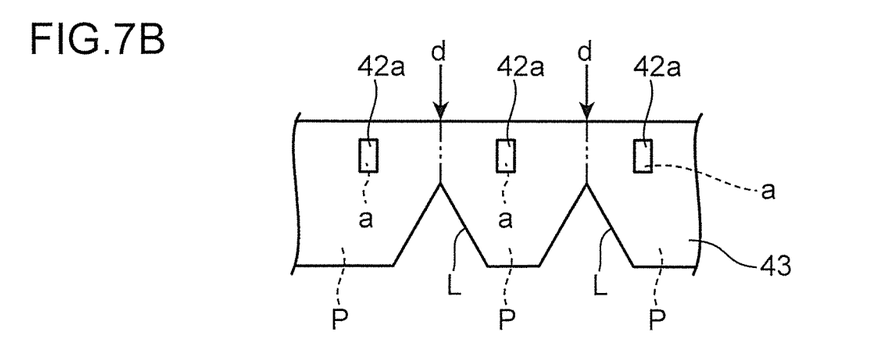
FIG. 7B is a plan view showing a state where strips of a first sheet are adhered onto a second sheet.

As shown in FIG. 7B, a composite sheet manufactured, for example, by the composite sheet manufacturing device of Japanese Unexamined Patent Publication No. 2007-259952 can be applied to disposable wearable articles P. Specifically, the disposable wearable articles P can be manufactured by forming leg holes L on the composite sheet, doubling the sheet in a width direction, welding parts of the sheet and cutting these welded parts at positions d.

Figure 7C:
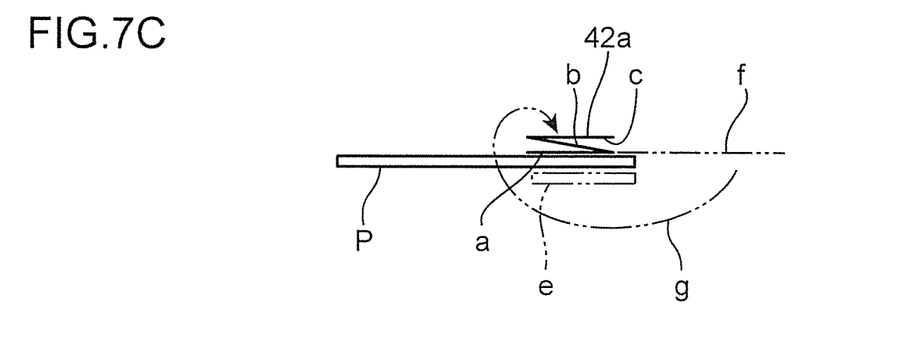
FIG. 7C is a side view of a disposable wearable article.

As shown in FIG. 7C, the strip 42a may be, for example, folded into an inverted Z shape and surfaces indicated by a, b and c in FIG. 7C may be adhesive surfaces. Note that the strips 42a used for the disposable wearable articles P are called disposable tapes or waste tapes.

In this case shown in FIG. 7C, the used wearable article P is folded as indicated by a chain double-dashed line e, the strip 42a is unfolded as indicated by a chain double-dashed line f and wound around the folded wearable article P as indicated by an arrow g and the adhesive surface c on a tip side of the strip 42a is adhered to the wearable article P. In this way, the used wearable article P can be hygienically disposed of in a compact form.

However, the first sheet 42 has the adhesive surface a and the cutter 40a of the cutter roller 40 needs to cut the adhesive surface a and the first sheet 42. Thus, when the cutter 40a comes to be heated, i.e. the temperature of the cutter 40a becomes high, the adhesive of the adhesive surface a easily adheres to the cutter 40a. Thus, there has been a problem that cutting performance of the cutter 40 is gradually reduced. Particularly, in the case of cutting the first sheet 42 from the side of the adhesive surface a, the adhesive more easily adheres to the cutter 40a.

SUMMARY OF INVENTION

The present invention was developed to solve the above problem and aims to provide a composite sheet manufacturing device and a composite sheet manufacturing method capable of maintaining high cutting performance of a cutter by suppressing the adhesion of an adhesive of an adhesive surface to the cutter.

To solve the above problem, the present invention provides a composite sheet manufacturing device for compounding strips produced from a first sheet and a second sheet, the first sheet having an adhesive surface, the device including a cutter roller configured to rotate about a predetermined axis and including a cutter, an anvil roller configured to cut the first sheet into strips by introducing the first sheet to between the cutter roller and the anvil roller by rotating relative to the cutter roller, and a cooling unit configured to cool at least one of the cutter of the cutter roller and the anvil roller by a refrigerant.

Further, the present invention provides a composite sheet manufacturing method for compounding strips produced by cutting a sheet-like first sheet having an adhesive surface and a sheet-like second sheet, the method including a cutting step of cutting the first sheet between a cutter provided on a cutter roller and an anvil roller to produce the strips by introducing the first sheet to between the anvil roller configured to rotate about a predetermined axis and the cutter roller configured to rotate relative to the anvil roller about a predetermined axis, and a cooling step of cooling at least one of the cutter of the cutter roller and the anvil roller by a refrigerant, the cooling step being performed at least during the execution of the cutting step.

According to the present invention, it is possible to maintain high cutting performance of a cutter by suppressing the adhesion of an adhesive of an adhesive surface to the cutter.

DESCRIPTION OF EMBODIMENT

Hereinafter, an embodiment of the present invention is described in detail with reference to the drawings. Note that components having the same configurations and functions as the conventional device are denoted by the same reference signs and not described in detail.

Figure 1:
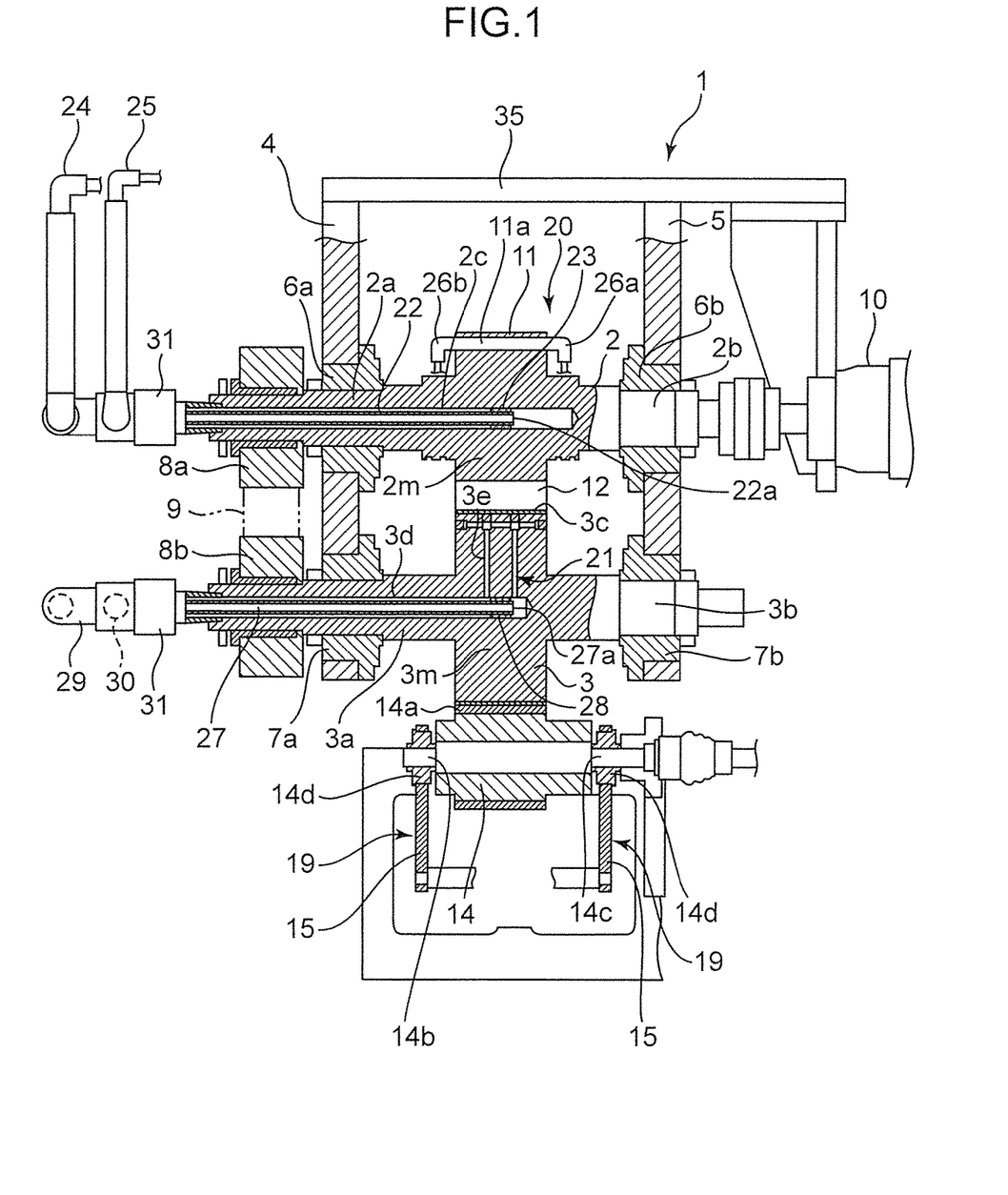
FIG. 1 is a front view in section of a composite sheet manufacturing device according to an embodiment of the present invention.
Figure 2:
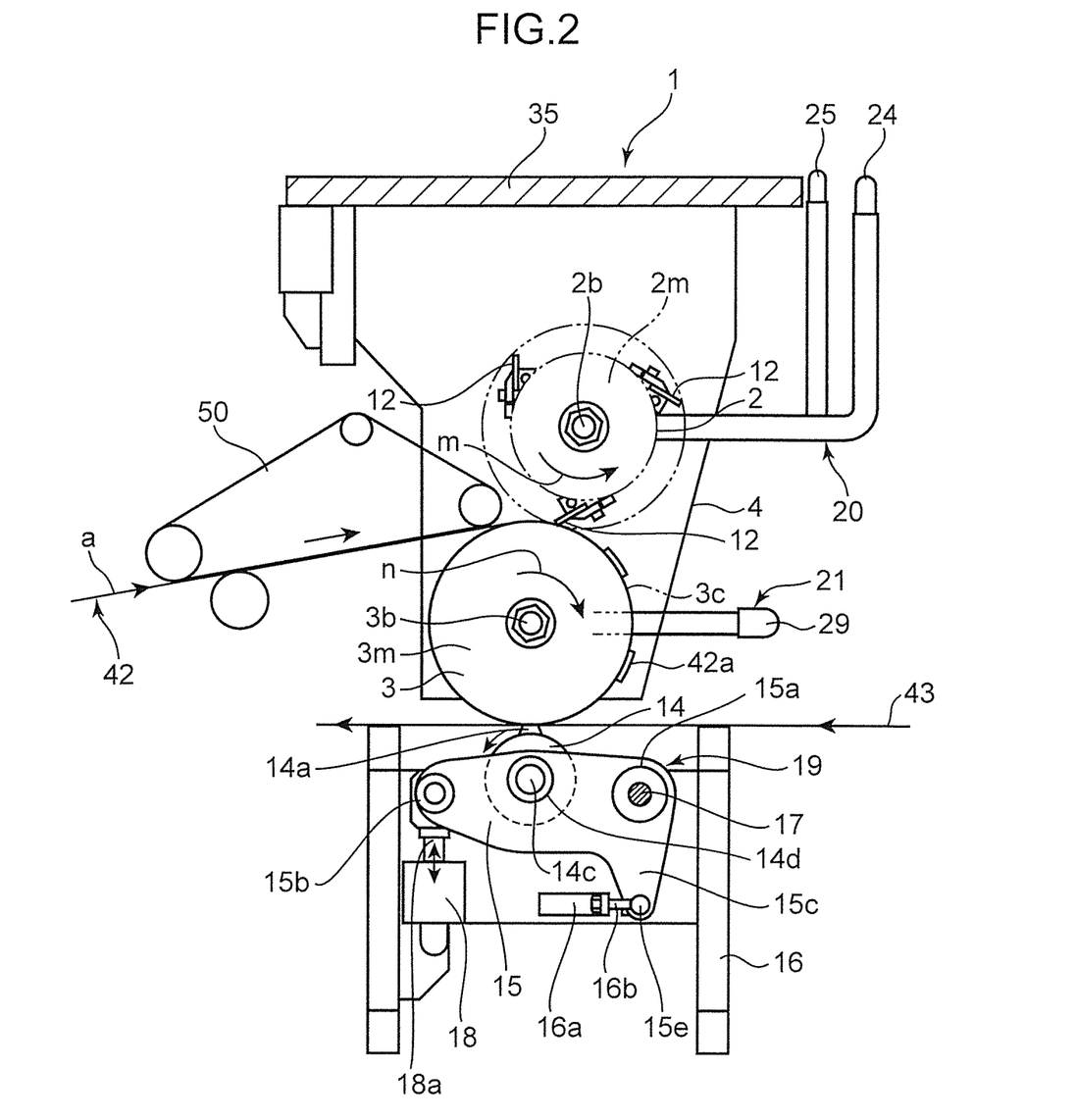
FIG. 2 is a side view in section of the composite sheet manufacturing device shown in FIG. 1.
Figure 3A:
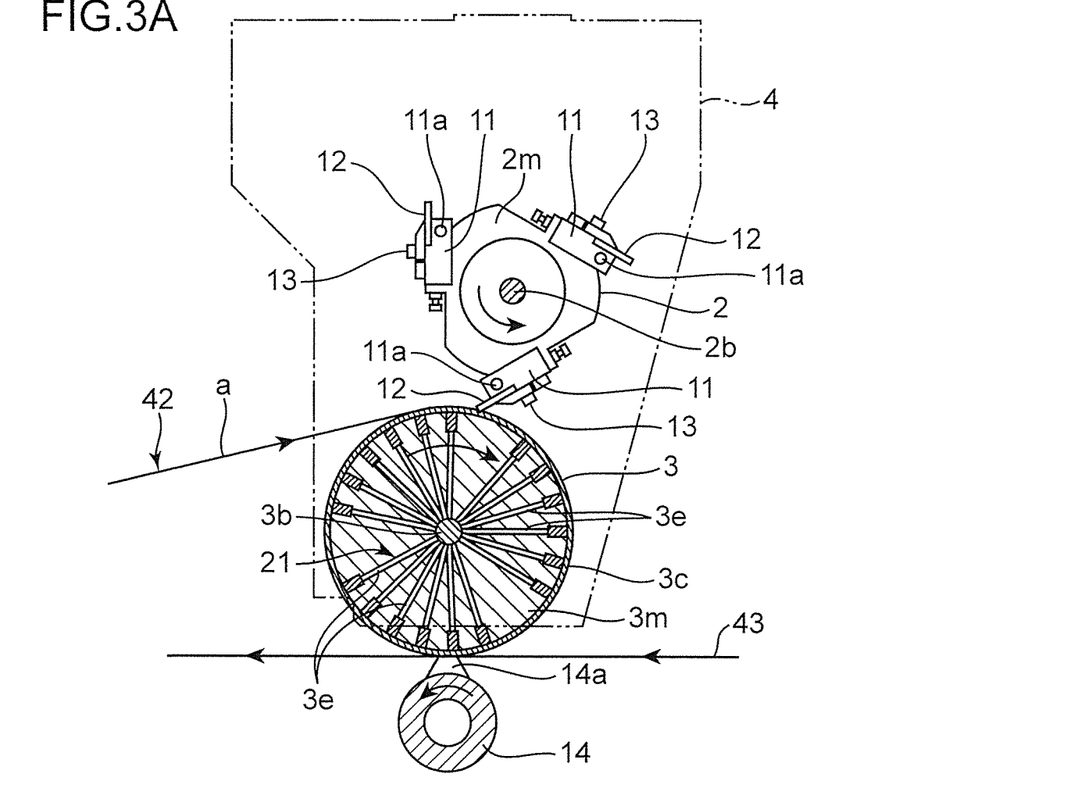
FIG. 3A is a side view in section of essential parts of a cutter roller and an anvil roller.
Figure 3B:
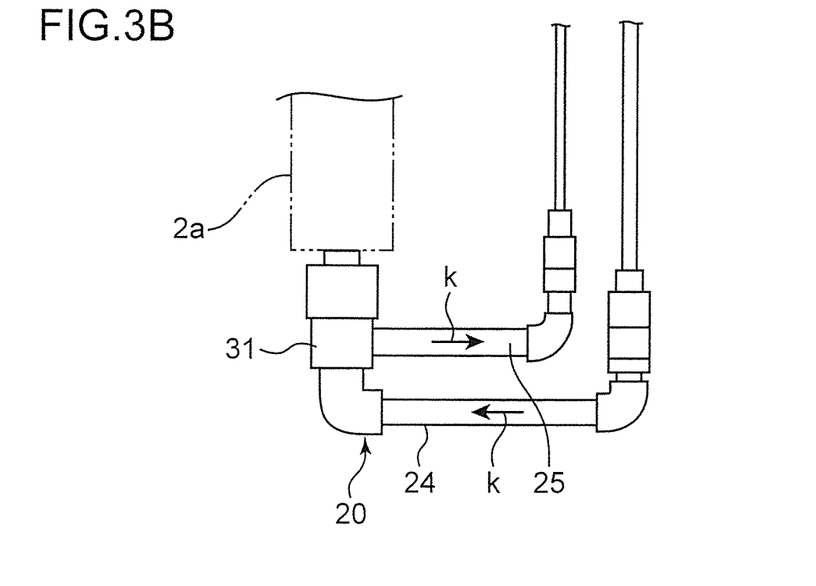
FIG. 3B is a plan view of a cutter-roller side refrigerant supply pipe and a cutter-roller side refrigerant discharge pipe.

FIG. 1 is a front view in section of a composite sheet manufacturing device 1 according to this embodiment. FIG. 2 is a side view in section of the composite sheet manufacturing device 1 shown in FIG. 1. FIG. 3A is a side view in section of essential parts of a cutter roller 2 and an anvil roller 3 and FIG. 3B is a plan view of a cutter-roller side refrigerant supply pipe 24 and a cutter-roller side refrigerant discharge pipe 25.

The composite sheet manufacturing device 1 includes the cutter roller 2, the anvil roller 3, a first vertical base plate 4 and a second vertical base plate 5 supporting these rollers, a first cooling unit 20, a second cooling unit 21, a press roller 14 and a pressing pressure adjustment mechanism 19.

The first and second vertical base plates 4, 5 are facing each other substantially in parallel.

The cutter roller 2 that rotates about a predetermined axis is arranged on an upper side and the anvil roller 3 that rotates about an axis extending in parallel to a rotary shaft of the cutter roller 2 is arranged on a lower side between the first and second vertical base plates 4 and 5.

The cutter roller 2 includes a main body 2m having cutters 12 to be described later mounted thereon and shaft portions 2a, 2b respectively extending outward from the opposite end surfaces of this main body 2m in a rotary shaft direction of the cutter roller 2. The cutter roller 2 is rotatably supported on the base plates 4, 5 by having these shaft portions 2a, 2b rotatably supported by a bearing 6a fixed to the first vertical base plate 4 and a bearing 6b fixed to the second vertical base plate 5.

The anvil roller 3 includes a substantially cylindrical main body 3m arranged at a position facing the main body of the cutter roller 2 and having a center axis, which is a rotary shaft of the anvil roller 3, and shaft portions 3a, 3b respectively extending outward from the opposite end surfaces of the main body 3m in a rotary shaft direction of the anvil roller 3. The anvil roller 3 is rotatably supported on the base plates 5, 6 by being rotatably supported by a bearing 7a fixed to the first vertical base plate 4 and a bearing 7b fixed to the second vertical base plate 5.

The cutter roller 2 and the anvil roller 3 are driven to rotate relative to each other, i.e. the cutter roller 2 and the anvil roller 3 are respectively driven to rotate counterclockwise (see a counterclockwise arrow m) and clockwise (see a clockwise arrow n) in synchronization at the same circumferential speed in FIG. 2. Specifically, a pulley 8a mounted on the outer periphery of the shaft portion 2a of the cutter roller 2 and a pulley 8b mounted on the outer periphery of the shaft portion 3a of the anvil roller 3 are coupled by a timing belt 9. The shaft portion 2b of the cutter roller 2 is driven by a motor 10, whereby the cutter roller 2 and the anvil roller 3 rotate in synchronization.

The main body 2m of the cutter roller 2 is formed into a triangular shape in a side view as shown in FIG. 3 and has three substantially flat surfaces. Cutter bases 11 are fixed to the respective surfaces (three surfaces). The cutter 12 is mounted on each cutter base 11 by a bolt 13.

The tip of the cutter 12 is mounted on the cutter base 11 to be able to cut a first sheet 42 and form a predetermined clearance between an outer peripheral surface 3c of the anvil roller 3 and the tip of the cutter 12 or come into contact with the outer peripheral surface 3c.

In the composite sheet manufacturing device 1 configured as described above, the cutter roller 2 and the anvil roller 3 rotate relative to each other, whereby the first sheet 42 is pulled in between the both rollers 2 and 3 and the cutter 12 comes into contact with the first sheet 42 between the rollers 2 and 3 to cut the first sheet 42 into a strip 42a.

Suction holes 3f (see FIG. 6) for temporarily sucking and holding the cut strips 42a are formed on the outer peripheral surface 3c of the anvil roller 3. The strips 42a are sucked and held on the outer peripheral surface of the anvil roller 3 via these suction holes 3f until adhesive surfaces a thereof to be described later are adhered onto a second sheet 43 and compounded with the second sheet 43.

An adhesive is applied to a surface of the first sheet 42 to be cut into the strips 42a by the cutters 12. Specifically, the first sheet 42 has the adhesive surface a having the adhesive applied thereto. The cutters 12 cut this adhesive surface a and the first sheet 42. The first sheet 42 is introduced to between the cutter roller 2 and the anvil roller 3 in a posture that the adhesive surface a faces toward the cutter roller 2 as shown in FIG. 2 and other figures. Thus, the first sheet 42 is cut by the cutters 12 from the side of the adhesive surface a. Thus, when the cutters 12 come to be heated, the adhesive of the adhesive surface a easily adheres to the cutters 12. Therefore, cutting performance of the cutters 12 is reduced.

As a measure against this, the composite sheet manufacturing device 1 according to this embodiment includes a first cooling unit 20 for cooling the cutters 12 by a refrigerant (e.g. coolant) and a second cooling unit 21 for cooling the anvil roller 3 by a refrigerant (e.g. coolant).

The first cooling unit 20 includes cutter-roller side refrigerant flowing parts 11a, a cutter-roller side center hole 2c, a cutter-roller side refrigerant introducing pipe 22, a cutter-roller side packing 23, a cutter-roller side refrigerant supply pipe 24, a cutter-roller side refrigerant discharge pipe 25 and communication pipes 26a, 26b.

Figure 4:
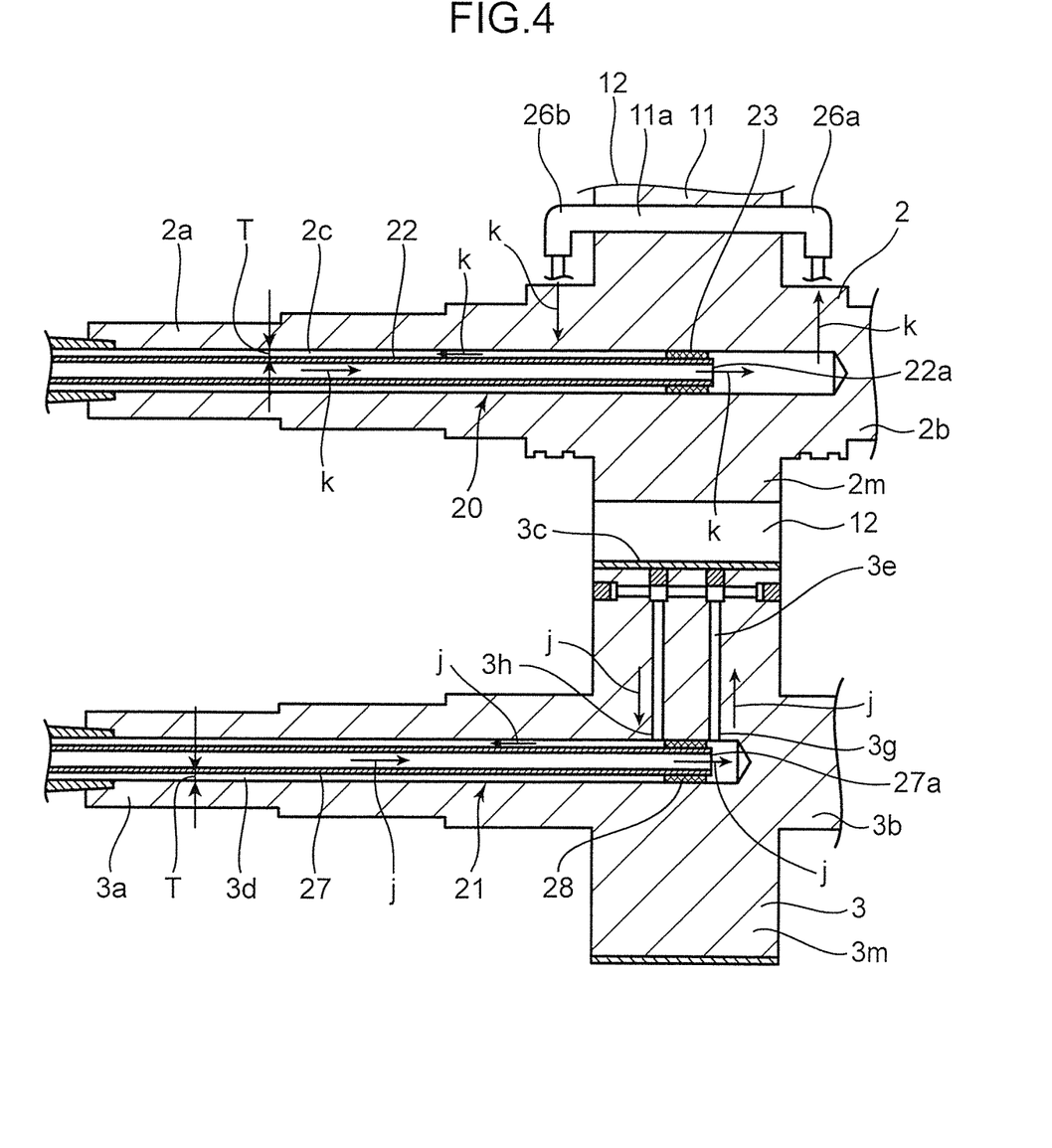
FIG. 4 is an enlarged view of an essential part of FIG. 1.

As shown in FIG. 4, the cutter-roller side center hole 2c is a hole formed inside the cutter roller 2. The cutter-roller side center hole 2c extends in the rotary shaft direction of the cutter roller 2. This cutter-roller side center hole 2c extends from one shaft portion 2a (left shaft portion 2a of FIG. 4) of the cutter roller 2 to the other shaft portion 2b (right shaft portion 2b of FIG. 4) through the main body of the cutter roller 2. This cutter-roller side center hole 2c is a bottomed hole and open only on an axial outer end surface of the one shaft portion 2a. In this embodiment, the cutter-roller side center hole 2c is closed at a position of the shaft portion 2b near the main body 2m of the cutter roller 2.

The cutter-roller side refrigerant introducing pipe 22 is for introducing the refrigerant into the cutter-roller side center hole 2c. The cutter-roller side refrigerant introducing pipe 22 is a pipe-like member and open on the opposite axial end parts thereof. The cutter-roller side refrigerant introducing pipe 22 extends along an axial direction of the cutter-roller side center hole 2c in the cutter-roller side center hole 2c. Specifically, the cutter-roller side refrigerant introducing pipe 22 extends from a base end located further outward than the shaft portion 2a of the cutter roller 2 to a predetermined position in the cutter-roller side center hole 2c.

The cutter-roller side refrigerant introducing pipe 22 includes a tip 22a arranged in the cutter-roller side center hole 2c and the refrigerant is introduced into the cutter-roller side center hole 2c from this tip 22a. The tip 22a of the cutter-roller side refrigerant introducing pipe 22, i.e. an end part of the cutter-roller side refrigerant introducing pipe 22 on the side of the shaft portion 2b, is arranged at a position inside the main body of the cutter roller 2 where the cutter bases 11 are mounted. The tip 22a of the cutter-roller side refrigerant introducing pipe 22 and the bottom surface of the cutter-roller side center hole 2c are separated. Further, a clearance T is formed between the outer peripheral surface of the cutter-roller side refrigerant introducing pipe 22 and the inner peripheral surface of the cutter-roller side center hole 2c.

The cutter-roller side packing 23 is a sealing member for sealing between the outer peripheral surface of the tip 22a (end part on the side of the shaft portion 2b) of the cutter-roller side refrigerant introducing pipe 22 and the inner peripheral surface of the cutter-roller side center hole 2c.

The cutter-roller side refrigerant supply pipe 24 is for supplying the refrigerant to the cutter-roller side refrigerant introducing pipe 22. As shown in FIGS. 1 and 3B, the cutter-roller side refrigerant supply pipe 24 is connected to the shaft portion 2a of the cutter roller 2 via a rotary joint 31. Further, the cutter-roller side refrigerant discharge pipe 25 is for discharging the refrigerant to the outside of the cutter roller 2. The cutter-roller side refrigerant discharge pipe 25 is connected to the shaft portion 2a of the cutter roller 2 via the rotary joint 31. The cutter-roller side refrigerant discharge pipe 25 communicates with the clearance T between the outer peripheral surface of the cutter-roller side refrigerant introducing pipe 22 and the inner peripheral surface of the cutter-roller side center hole 2c, and leads the refrigerant in this clearance T to outside.

The cutter-roller side refrigerant flowing parts 11a are parts in which the refrigerant flows. Specifically, the cutter-roller side refrigerant flowing parts 11a are through holes penetrating through the cutter bases 11 and open on the opposite end surfaces of the cutter bases 11 in the rotary shaft direction of the cutter roller 2.

The communication pipes 26a, 26b respectively allow communication between the cutter-roller side center hole 2c and the respective openings of the cutter-roller side refrigerant flowing part 11a.

One communication pipe 26a allows communication between the entrance (one opening) of the cutter-roller side refrigerant flowing part 11a and a part of the inner space of the cutter-roller side center hole 2c closer to the tip 22a (shaft portion 2b) of the cutter-roller side refrigerant introducing pipe 22 than the cutter-roller side packing 23.

The other communication pipe 26b allows communication between the exit (other opening) of the cutter-roller side refrigerant flowing part 11a and a part of the inner space of the cutter-roller side center hole 2c closer to a base end (shaft portion 2a) of the cutter-roller side refrigerant introducing pipe 22 than the cutter-roller side packing 23. Specifically, the communication pipe 26b communicates with the exit of the cutter-roller side refrigerant flowing part 11a and a part between the outer peripheral surface of the cutter-roller side refrigerant introducing pipe 22 and the inner peripheral surface of the cutter-roller side center hole 2c.

In the first cooling unit 20 configured as described above, the refrigerant k is introduced into a part of the cutter-roller side center hole 2c closer to the tip 22a than the cutter-roller side packing 23 from the tip 22a of the cutter-roller side refrigerant introducing pipe 22 by the cutter-roller side refrigerant supply pipe 24. This refrigerant k is introduced into the cutter-roller side refrigerant flowing parts 11a from the entrances of the cutter-roller side refrigerant flowing parts 11a via the communication pipes 26a and flows in the cutter-roller side refrigerant flowing parts 11a. The cutter bases 11 and the cutters 12 are cooled by the flow of this refrigerant k. Thereafter, the refrigerant k is introduced into the cutter-roller side center hole 2c via the communication pipes 26b from the exits of the cutter-roller side refrigerant flowing parts 11a. Specifically, the refrigerant k is led out into the clearance T between the inner peripheral surface of the cutter-roller side center hole 2c and the outer peripheral surface of the cutter-roller side refrigerant introducing pipe 22 in the part of the cutter-roller side center hole 2c closer to the base end of the cutter-roller side refrigerant introducing pipe 22 than the cutter-roller side packing 23. Thereafter, the refrigerant k is discharged to the outside of the cutter roller 2 by the cutter-roller side refrigerant discharge pipe 25.

As just described, in this device, the cutters 12 of the cutter roller 2 are cooled by the refrigerant by the first cooling unit 20, whereby the cutters 12 are not heated, i.e. it is avoided that the cutters 12 have a high temperature. Thus, the adhesive of the first sheet 42 is not adhered to the cutters 12, wherefore high cutting performance of the cutters 12 can be maintained. As a result, the first sheet 42 can be constantly neatly cut even from the side of the adhesive surface a.

Particularly, in this embodiment, the refrigerant to be led out from the cutter bases 11 flows around the low-temperature refrigerant in the cutter-roller side refrigerant introducing pipe 22 to be introduced into the cutter bases 11 in the cutter-roller side center hole 2c. Thus, the low-temperature refrigerant on the introducing side is shut off from the heat of the cutter roller 2 by the refrigerant on the lead-out side and maintained at a low temperature, wherefore cooling efficiency of the cutters 12 of the cutter roller 2 is improved.

The second cooling unit 21 includes anvil-roller side refrigerant flowing parts 3e, an anvil-roller side center hole 3d, an anvil-roller side refrigerant introducing pipe 27, an anvil-roller side packing 28, an anvil-roller side refrigerant supply pipe 29 and an anvil-roller side refrigerant discharge pipe 30.

As shown in FIG. 4, the anvil-roller side center hole 3d is a hole formed inside the anvil roller 3. The anvil-roller side center hole 3d extends in the rotary shaft direction of the anvil roller 3. This anvil-roller side center hole 3d is a bottomed hole extending from one shaft portion 3a (left shaft portion 3a of FIG. 4) of the anvil roller 3 to the interior of the main body of the anvil roller 3 and open only on an axial outer end surface of the one shaft portion 3a.

The anvil-roller side refrigerant introducing pipe 27 is for introducing the refrigerant into the anvil-roller side center hole 3d. The anvil-roller side refrigerant introducing pipe 27 is a pipe-like member and open on the opposite axial end parts thereof. The anvil-roller side refrigerant introducing pipe 27 extends along an axial direction of the anvil-roller side center hole 3d in the anvil-roller side center hole 3d. Specifically, the anvil-roller side refrigerant introducing pipe 27 extends from a base end located further outward than the shaft portion 3a of the anvil roller 3 to a predetermined position in the anvil-roller side center hole 3d.

The anvil-roller side refrigerant introducing pipe 27 includes a tip 27a arranged in the anvil-roller side center hole 3d and the refrigerant is introduced into the anvil-roller side center hole 3d from this tip 27a. The tip 27a of the anvil-roller side refrigerant introducing pipe 27, i.e. an end part of the anvil-roller side refrigerant introducing pipe 27 on the side of the shaft portion 3b, is located in an axial intermediate part of the main body 3m of the anvil roller 3 and separated from the bottom surface of the anvil-roller side center hole 3d. Further, a clearance T is formed between the outer peripheral surface of the anvil-roller side refrigerant introducing pipe 27 and the inner peripheral surface of the anvil-roller side center hole 3d.

The anvil-roller side packing 28 is a sealing member for sealing between the outer peripheral surface of the tip 27a (end part on the side of the shaft portion 3b) of the anvil-roller side refrigerant introducing pipe 27 and the inner peripheral surface of the anvil-roller side center hole 3d.

The anvil-roller side refrigerant supply pipe 29 is for supplying the refrigerant to the anvil-roller side refrigerant introducing pipe 27. The anvil-roller side refrigerant supply pipe 29 is connected to the shaft portion 3a of the anvil roller 3 via a rotary joint 31. Further, the anvil-roller side refrigerant discharge pipe 30 is for discharging the refrigerant to the outside of the anvil roller 3. The anvil-roller side refrigerant discharge pipe 30 is connected to the shaft portion 3a of the anvil roller 3 via the rotary joint 31. The anvil-roller side refrigerant discharge pipe 30 communicates with the clearance T between the outer peripheral surface of the anvil-roller side refrigerant introducing pipe 27 and the inner peripheral surface of the anvil-roller side center hole 3d, and leads the refrigerant in this clearance T to outside.

The anvil-roller side refrigerant flowing parts 3e are parts in which the refrigerant flows and formed in the main body 3m of the anvil roller 3. Each anvil-roller side refrigerant flowing part 3e includes an entrance 3g for introducing the refrigerant from outside and an exit 3h for discharging the refrigerant to outside. In this embodiment, a multitude of anvil-roller side refrigerant flowing parts 3e are radially formed at a predetermined angular interval as shown in FIG. 3A. The entrance 3g of each anvil-roller side refrigerant flowing part 3e communicates with the anvil-roller side center hole 3d at a position closer to the tip 27a (shaft portion 3b) of the anvil-roller side refrigerant introducing pipe 27 than the anvil-roller side packing 28. The exit 3h of the anvil-roller side refrigerant flowing part 3e communicates with the anvil-roller side center hole 3d at a position closer to a base end (shaft portion 3a) of the anvil-roller side refrigerant introducing pipe 27 than the anvil-roller side packing 28. As shown in FIG. 4, the anvil-roller side refrigerant flowing part 3e includes parts extending from the entrance 3g and the exit 3h thereof in a radial direction of the anvil roller 3 toward the outer peripheral surface of the anvil roller 3 and has an inverted U shape. Specifically, after extending from a center axis of the main body of the anvil roller 3 toward the outer peripheral surface 3c of the anvil roller 3, the anvil-roller side refrigerant flowing part 3e extends in parallel to the center axis of the anvil roller 3 along the outer peripheral surface 3c and then extends toward the center axis of the anvil roller 3.

In the second cooling unit 21 configured as described above, the refrigerant j is introduced into a part of the anvil-roller side center hole 3d closer to the tip 27a (shaft portion 3b) of the anvil-roller side refrigerant introducing pipe 27 than the anvil-roller side packing 28 from the tip 27a of the anvil-roller side refrigerant introducing pipe 27 by the anvil-roller side refrigerant supply pipe 29. This refrigerant j is introduced into the anvil-roller side refrigerant flowing parts 3e from the entrances 3g of the anvil-roller side refrigerant flowing parts 3e and flows in the anvil-roller side refrigerant flowing parts 3e. The outer peripheral surface 3c of the anvil roller 3 is cooled by the flow of this refrigerant j. Thereafter, the refrigerant j is introduced into the anvil-roller side center hole 3d from the exits 3h of the anvil-roller side refrigerant flowing parts 3e. Specifically, the refrigerant j is led out into the clearance T between the inner peripheral surface of the anvil-roller side center hole 3d and the outer peripheral surface of the anvil-roller side refrigerant introducing pipe 27 in a part of the anvil-roller side center hole 3d closer to the base end (shaft portion 3b) of the anvil-roller side refrigerant introducing pipe 27 than the anvil-roller side packing 28. Thereafter, the refrigerant j is discharged to the outside of the anvil roller 3 by the anvil-roller side refrigerant discharge pipe 30.

As just described, in this device, the anvil roller 3 is cooled by the refrigerant by the second cooling unit 21, whereby heat of the anvil roller 3 is not transferred to the cutters 12 of the cutter roller 2. Specifically, it is suppressed that the cutters 12 are heated by the anvil roller 3. In this way, it is suppressed that the cutters 12 have a high temperature. Thus, the adhesive of the first sheet 42 is not adhered to the cutters 12, wherefore high cutting performance of the cutters 12 can be maintained. As a result, the first sheet 42 can be constantly neatly cut even from the side of the adhesive surface a.

Particularly, in this embodiment, the refrigerant to be led out from the anvil-roller side refrigerant flowing parts 3e flows around the low-temperature refrigerant in the anvil-roller side refrigerant introducing pipe 27 to be introduced into the anvil-roller side refrigerant flowing parts 3e in the anvil-roller side center hole 3d. Thus, the low-temperature refrigerant on the introducing side is shut off from the heat of the anvil roller 3 by the refrigerant on the lead-out side and maintained at a low temperature, wherefore cooling efficiency of the anvil roller 3 is improved.

As just described, in this embodiment, a cooling step of cooling at least either the cutters 12 of the cutter roller 2 or the anvil roller 3 by the refrigerant is performed while performing a cutting step of introducing the first sheet 42 to between the anvil roller 3 and the cutter roller 2 and cutting the first sheet 42 by the cutters 12 provided on the cutter roller 2 to produce the strips 42a. In this way, it can be suppressed that the cutters 12 have a high temperature and high cutting performance of the cutters 12 can be maintained.

Note that although the first cooling unit 20 for the cutter roller 2 and the second cooling unit 21 for the anvil roller 3 are provided in the above embodiment, only either one of them may be provided.

Next, the press roller 14 and the pressing pressure adjustment mechanism 19 are described.

The press roller 14 is for pressing the strips 42a adhered onto the second sheet 43 against the outer peripheral surface 3c of the anvil roller 3 via the second sheet 43.

The pressing pressure adjustment mechanism 19 is for adjusting this pressing pressure. In this embodiment, the pressing pressure adjustment mechanism 19 includes a pair of brackets 15, 15, cylinders 18, piston rods 18a and stoppers 16a.

The press roller 14 is a substantially cylindrical member centered on an axis parallel to the rotary shaft of the anvil roller 3 and rotated and driven about this center axis in synchronization with the rotation of the cutter roller 2 and the anvil roller 3. The press roller 14 is arranged below the anvil roller 3. The press roller 14 rotates relative to the anvil roller 3. That is, the anvil roller 3 rotates clockwise in FIG. 2, whereas the press roller 14 rotates counterclockwise. The second sheet 43, to which the strips 42a are to be adhered, is pulled in between the press roller 14 and the anvil roller 3 with the relative rotation of these rollers 14, 3. The strips 42a move toward the press roller 14 with the rotation of the anvil roller 3 and are adhered to the second sheet 43 between the press roller 14 and the anvil roller 3.

As shown in FIGS. 1 and 2, a cushioning projection 14a for pressing the strip 42a against the outer peripheral surface of the anvil roller 3 via the second sheet 43 with pinpoint accuracy is provided on the outer peripheral surface of the press roller 14. This projection 14a projects radially outwardly from the outer peripheral surface of a cylindrical part of the press roller 14. The press roller 14 presses the strip 42a against the outer peripheral surface of the anvil roller 3 via the second sheet 43 by the tip of the projection 14a.

A frame 16 is a frame member for supporting the press roller 14.

The respective brackets 15, 15 are for rotatably supporting the press roller 14. Specifically, the press roller 14 is supported on the frame 16 via the brackets 15, 15.

As shown in FIG. 1, the brackets 15, 15 respectively rotatably support opposite end parts 14b, 14c of the press roller 14 in a center axis direction via bearings 14d. As shown in FIG. 2, the brackets 15, 15 are shaped to extend in a direction in which the second sheet 43 is conveyed, i.e. a conveying direction of the second sheet 43. The bearing 14d is arranged between one end part 15a and the other end part 15b of the bracket 15 in a direction parallel to the conveying direction of the second sheet 43.

Each bracket 15 is supported on the frame 16 in such a state to be vertically swingable with the one end part 15a thereof as a supporting point. Specifically, each bracket 15 is vertically swingably supported by a hinge shaft (supporting portion) 17 mounted on the one end part 15a thereof. The hinge shaft 17 is arranged below the anvil roller 3 in the frame 16.

The piston rod 18a is for pressing the bracket 15. The piston rod 18a is arranged below the other end part 15b of each bracket 15 and presses this other end part 15b upwardly. The piston rod 18a is vertically movably inserted into the cylinder 18. The cylinder 18 is supported by the frame 16.

The stopper 16a is for specifying a swing position of the bracket 15. Specifically, the stopper 16a can regulate a swinging movement of the bracket 15 with the bracket 15 swung to a predetermined regulating position and change this regulating position. The stopper 16a is provided on the frame 16. Specifically, the bracket 15 includes a shaft 15e on a lower end part 15c thereof and the stopper 16a includes a bolt 16b projecting toward this shaft 15e. The stopper 16a regulates the swinging movement of the bracket 15 by the contact of the shaft 15e and a tip part of the bolt 16b. In this embodiment, the stopper 16a comes into contact with the shaft 15e to regulate an upward swinging movement of the other end part 15b of the bracket 15 beyond this contact position. In this way, it is avoided that the pressing pressure of the press roller 14 becomes excessive. Here, the bolt 16b is screwed into a stopper main body (denoted by no reference sign) and a projecting amount of the bolt 16b from the stopper main body toward the shaft 15e is changed by changing a screwing amount. Thus, the swing position (regulating position where the swinging movement is regulated by the stopper) of each bracket 15 is changed by adjusting the screwing amount of the bolt 16b.

In the pressing pressure adjustment mechanism 19 configured as described above, when the piston rods 18a of the cylinders 18 push up the other end parts 15b of the respective brackets 15, the other end parts 15b of the respective brackets 15 swing upwardly about the hinge shafts 17 (one end parts 15a). Associated with this, the press roller 14 supported on the respective brackets 15 moves upwardly. This causes the projection 14a of the press roller 14 to press the strip 42a against the outer peripheral surface of the anvil roller 3 via the second sheet 43 with pinpoint accuracy.

Here, as described above, the stopper 16a can regulate the swing position (regulating positon) of each bracket 15 and, consequently, a vertical position of the press roller 14 by adjusting the screwing amount of the bolt 16b. Thus, the pressing pressure of the press roller 14 can be adjusted by adjusting this screwing amount.

Accordingly, even if thicknesses of strips 42a of the first sheet 42 and the second sheet 43 change, the pressing pressure can be adjusted so that the strips 42a are pressed with a proper pressing pressure. This enables the adhesive surfaces a of the strips 42a to be firmly adhered to the second sheet 43.

Further, if forces of the piston rods 18a for pressing the other end parts 15b of the brackets 15 are set at a proper value and the piston rods 18a are vertically displaceably supported by the cylinders 18, the piston rods 18a can be automatically vertically displaced according to the thicknesses of the strip 42a and the second sheet 43 introduced to between the anvil roller 3 and the press roller 14, whereby the vertical position of the press roller 14 can be automatically changed to a proper position corresponding to the thicknesses while the pressing pressure is properly maintained.

Note that although the brackets 15 are pressed by the piston rods 18a in the above embodiment, members for pressing the brackets 15 are not limited to these. For example, spring members may be used instead of the cylinders 18 and the piston rods 18a.

Note that, in the conventional device shown in FIG. 7A, the adhesive is applied to the first sheet 42 by the coating unit 46 on the carrying conveyor 45. Contrary to this, in this embodiment, the carrying conveyor 50 is arranged above the first sheet 42 and the first sheet 42 is conveyed in such a posture that the adhesive surface a is faced up by this carrying conveyor 50 as shown in FIG. 2. Thus, the adhesive surface a of the first sheet 42 may adhere to the carrying conveyor 50. Accordingly, in this embodiment, silicon coating is applied to the outer surface of the carrying conveyor 50 to prevent the adhesion of the adhesive surface a to the carrying conveyor 50.

Further, in this embodiment, the cutter roller 2, the anvil roller 3 and the like are integrated into a cutter unit by integrally coupling upper parts of the first and second vertical base plates 4, 5 by a ceiling plate 35.

Figure 5:
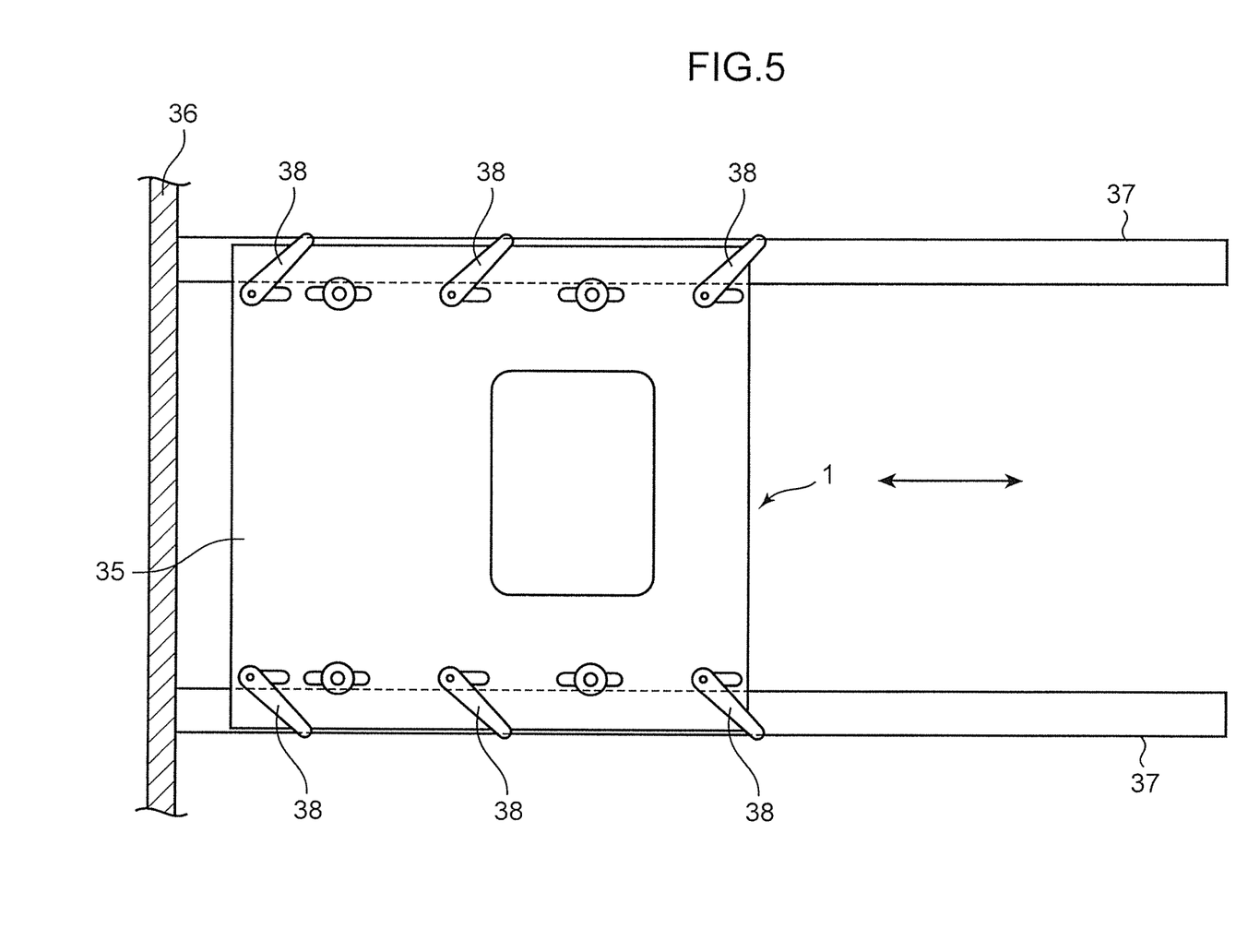
FIG. 5 is a plan view of a cutter unit including the cutter roller, the anvil roller and the like when viewed from a ceiling plate side.
Figure 6:
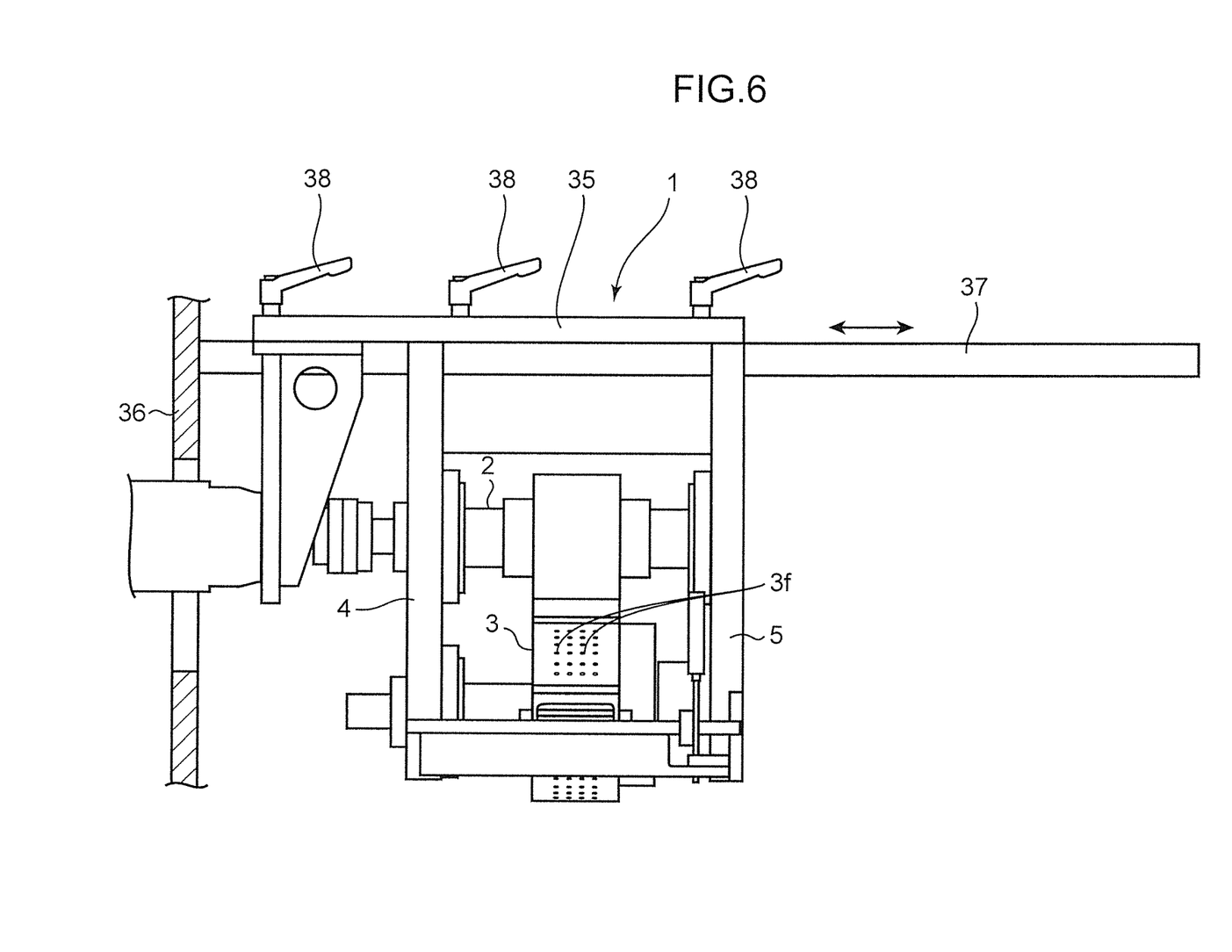
FIG. 6 is a front view of FIG. 5.

A pair of beam members 37 extending in a direction perpendicular to a production line is supported in a cantilever manner on a supporting frame 36 extending along the production line as shown in FIGS. 5 and 6. This pair of beam members 37 support the ceiling plate 35. This enables the unitized cutter roller 2, anvil roller 3 and like to reciprocate (see arrows of FIG. 5) along the direction perpendicular to the production line along the pair of beam members 37.

Movements of these unitized cutter roller 2, anvil roller 3 and like are used in finely adjusting a cutting position of the first sheet 42 and an adhering position of the strip 42a to the second sheet 43.

Further, if the unitized cutter roller 2, anvil roller 3 and like are moved to ends of the pair of beam members 37 deviated from the production line, maintenance can be easily performed for the cutter roller 2, the anvil roller 3 and the like outside the production line.

A plurality of lock levers 38 are mounted on the ceiling plate 35. By manually operating these lock levers 38, the pair of beam members 37 can be locked lest the ceiling plate 35 should inadvertently move.

Note that the specific embodiment described above mainly includes inventions having the following configurations.

Specifically, the present invention provides a composite sheet manufacturing device for compounding strips produced from a first sheet and a second sheet, the first sheet having an adhesive surface, the composite sheet manufacturing device including a cutter roller configured to rotate about a predetermined axis and including a cutter, an anvil roller configured to cut the first sheet into strips by introducing the first sheet to between the cutter roller and the anvil roller by rotating relative to the cutter roller, and a cooling unit configured to cool at least one of the cutter of the cutter roller and the anvil roller by a refrigerant.

According to the present invention, at least one of the cutter of the cutter roller and the anvil roller is cooled by the refrigerant by the cooling unit, whereby the cutter is not heated, i.e. it is suppressed that the cutter has a high temperature. Thus, the adhesion of an adhesive of the first sheet to the cutter is suppressed, wherefore high cutting performance of the cutter can be maintained. As a result, the first sheet can be constantly neatly cut even if being cut from the side of the adhesive surface.

The cooling unit preferably includes a cutter-roller side refrigerant flowing part formed in the cutter roller and configured such that the refrigerant flows inside.

According to this configuration, the cutter can be cooled by the refrigerant.

Preferably, the cooling unit includes a cutter-roller side center hole formed inside the cutter roller and extending in a rotary shaft direction of the cutter roller, a cutter-roller side refrigerant introducing pipe extending along an axial direction of the cutter-roller side center hole in the cutter-roller side center hole with a clearance defined between an inner peripheral surface of the cutter-roller side center hole and the cutter-roller side refrigerant introducing pipe and having a tip arranged in the cutter-roller side center hole to introduce the refrigerant into the cutter-roller side center hole, and a cutter-roller side packing configured to seal between an outer peripheral surface of the tip of the cutter-roller side refrigerant introducing pipe and the inner peripheral surface of the cutter-roller side center hole, the cutter-roller side refrigerant flowing part includes an entrance for introducing the refrigerant into the cutter-roller side refrigerant flowing part from outside and an exit for discharging the refrigerant to the outside of the cutter-roller side refrigerant flowing part, the entrance of the cutter-roller side refrigerant flowing part communicates with the cutter-roller side center hole at a position closer to the tip of the cutter-roller side refrigerant introducing pipe than the cutter-roller side packing and the exit of the cutter-roller side refrigerant flowing part communicates with the cutter-roller side center hole at a position closer to a base end of the cutter-roller side refrigerant introducing pipe than the cutter-roller side packing.

According to this configuration, the refrigerant introduced into the part of the cutter-roller side center hole closer to the tip of the cutter-roller side refrigerant introducing pipe than the packing from the cutter-roller side refrigerant introducing pipe is introduced into the cutter-roller side refrigerant flowing part from the entrance of the cutter-roller side refrigerant flowing part for the cutter and cools the cutter via the cutter-roller side refrigerant flowing part. Thereafter, the refrigerant is led out to the part of the cutter-roller side center hole closer to the base end of the cutter-roller side refrigerant introducing pipe than the packing from the exit of the cutter-roller side refrigerant flowing part and discharged to the outside. Thus, the low-temperature refrigerant on an introducing side is shut off from heat of the cutter roller by the refrigerant on a lead-out side, wherefore cooling efficiency of the cutter of the cutter roller is improved.

The cooling unit preferably includes an anvil-roller side refrigerant flowing part formed in the anvil roller and configured such that the refrigerant flows inside.

According to this configuration, the anvil roller can be cooled by the refrigerant.

Preferably, the cooling unit includes an anvil-roller side center hole formed inside the anvil roller and extending in a rotary shaft direction of the anvil roller, an anvil-roller side refrigerant introducing pipe extending along an axial direction of the anvil-roller side center hole in the anvil-roller side center hole with a clearance defined between an inner peripheral surface of the anvil-roller side center hole and the anvil-roller side refrigerant introducing pipe and having a tip arranged in the anvil-roller side center hole to introduce the refrigerant into the anvil-roller side center hole, and an anvil-roller side packing configured to seal between an outer peripheral surface of the tip of the anvil-roller side refrigerant introducing pipe and the inner peripheral surface of the anvil-roller side center hole, the anvil-roller side refrigerant flowing part includes an entrance for introducing the refrigerant into the anvil-roller side refrigerant flowing part from outside and an exit for discharging the refrigerant to the outside of the anvil-roller side refrigerant flowing part, the entrance of the anvil-roller side refrigerant flowing part communicates with the anvil-roller side center hole at a position closer to the tip of the anvil-roller side refrigerant introducing pipe than the anvil-roller side packing, the exit of the anvil-roller side refrigerant flowing part communicates with the anvil-roller side center hole at a position closer to a base end of the anvil-roller side refrigerant introducing pipe than the anvil-roller side packing and the anvil-roller side refrigerant flowing part includes parts extending in a radial direction of the anvil roller from the entrance and the exit thereof toward an outer peripheral surface of the anvil roller.

According to this configuration, the refrigerant introduced into the part of the anvil-roller side center hole closer to the tip of the anvil-roller side refrigerant introducing pipe than the packing from the tip of the anvil-roller side refrigerant introducing pipe is introduced into the anvil-roller side refrigerant flowing part from the entrance of the anvil-roller side refrigerant flowing part and cools the outer peripheral surface of the anvil roller via the anvil-roller side refrigerant flowing part. Thereafter, the refrigerant is led out to the part of the anvil-roller side center hole closer to the base end of the anvil-roller side refrigerant introducing pipe than the packing from the exit of the anvil-roller side refrigerant flowing part and discharged to the outside. Since the low-temperature refrigerant on an introducing side is shut off from heat of the anvil roller by the refrigerant on a lead-out side, cooling efficiency of the anvil roller is improved.

Here, the press roller 14 is for firmly adhering the adhesive surfaces a of the strips 42*a* to the second sheet 43. However, in the conventional device shown in FIG. 7A as disclosed in patent literature 1, there has been a problem that the strips 42*a* cannot be pressed with a proper pressing pressure if the thicknesses of the strips 42*a* and the second sheet 43 change.

Accordingly, the above composite sheet manufacturing device preferably further includes a press roller configured to press the strips adhered onto the second sheet against the outer peripheral surface of the anvil roller via the second sheet and a pressing pressure adjustment mechanism capable of adjusting a pressing pressure of the press roller against the anvil roller.

According to this configuration, the pressing pressure of the press roller against the anvil roller can be adjusted to a proper pressing pressure even if the thicknesses of the strips of the first sheet and the second sheet change. This enables the strips to be firmly adhered to the second sheet.

Here, the pressing pressure adjustment mechanism preferably includes a bracket configured to support the press roller rotatably about a center axis of the press roller, a supporting portion configured to support the bracket swingably about an axis parallel to a center axis of the press roller, and a stopper capable of regulating a swinging movement of the bracket with the bracket swung to a predetermined regulating position and changing the regulating position.

According to this configuration, the pressing pressure of the press roller can be adjusted by a simple configuration of providing the bracket, the supporting portion and the stopper for the press roller.

Further, the pressing pressure adjustment mechanism preferably includes a pressing member configured to press the bracket in a direction to swing the bracket toward the regulating position.

According to this configuration, the press roller can be pressed via the bracket by the pressing member (e.g. a cylinder or a spring).

Further, the present invention provides a composite sheet manufacturing method for compounding strips produced by cutting a sheet-like first sheet having an adhesive surface and a sheet-like second sheet, the method including a cutting step of cutting the first sheet between a cutter provided on a cutter roller and an anvil roller to produce the strips by introducing the first sheet to between the anvil roller configured to rotate about a predetermined axis and the cutter roller configured to rotate relative to the anvil roller about a predetermined axis, and a cooling step of cooling at least one of the cutter of the cutter roller and the anvil roller by a refrigerant, the cooling step being performed at least during the execution of the cutting step.

According to this method, it is suppressed that the cutter has a high temperature by cooling at least one of the cutter of the cutter roller and the anvil roller by the refrigerant by a cooling step. Thus, the adhesion of the adhesive surface of the first sheet to the cutter is suppressed, wherefore high cutting performance of the cutter can be maintained. As a result, the first sheet can be constantly neatly cut even if being cut from the side of the adhesive surface.

The invention claimed is:

1. A composite sheet manufacturing device for compounding strips produced from a first sheet and a second sheet, the first sheet having an adhesive surface, the device comprising:
    a cutter roller configured to rotate about a predetermined axis and including a main body and a cutter mounted thereon and shaft portions respectively extending outward from opposite end surfaces of the main body in a rotary shaft direction of the cutter roller;
    an anvil roller configured to cut the first sheet into strips by introducing the first sheet to between the cutter roller and the anvil roller by rotating relative to the cutter roller; and
    a cooling unit configured to cool at least one of the anvil roller and the cutter of the cutter roller by a refrigerant, the cooling unit including:
        a cutter-roller side refrigerant flowing part formed in the cutter roller and configured such that the refrigerant flows inside;
        a cutter-roller side center hole formed inside the main body of the cutter roller and extending in a rotary shaft direction of the cutter roller;
        a cutter-roller side refrigerant introducing pipe extending along an axial direction of the cutter-roller side center hole in the cutter-roller side center hole with a clearance defined between an inner peripheral surface of the cutter-roller side center hole and the cutter-roller side refrigerant introducing pipe and having a tip arranged in the cutter-roller side center hole to introduce the refrigerant into the cutter-roller side center hole; and
        a cutter-roller side packing configured to seal between an outer peripheral surface of the tip of the cutter-roller side refrigerant introducing pipe and the inner peripheral surface of the cutter-roller side center hole, wherein
    the cutter-roller side refrigerant flowing part includes an entrance for introducing the refrigerant into the cutter-roller side refrigerant flowing part from outside and an exit for discharging the refrigerant to the outside of the cutter-roller side refrigerant flowing part; and
    the entrance of the cutter-roller side refrigerant flowing part communicates with the cutter-roller side center hole at a position closer to the tip of the cutter-roller side refrigerant introducing pipe than the cutter-roller side packing and the exit of the cutter-roller side refrigerant flowing part communicates with the cutter-roller side center hole at a position closer to a base end of the cutter-roller side refrigerant introducing pipe than the cutter-roller side packing.

2. A composite sheet manufacturing device according to claim 1, wherein the cooling unit includes an anvil-roller side refrigerant flowing part formed in the anvil roller and configured such that the refrigerant flows inside.

3. A composite sheet manufacturing device according to claim 2,
    the cooling unit including:
    an anvil-roller side center hole formed inside the anvil roller and extending in a rotary shaft direction of the anvil roller;
    an anvil-roller side refrigerant introducing pipe extending along an axial direction of the anvil-roller side center hole in the anvil-roller side center hole with a clearance defined between an inner peripheral surface of the anvil-roller side center hole and the anvil-roller side refrigerant introducing pipe and having a tip arranged in the anvil-roller side center hole to introduce the refrigerant into the anvil-roller side center hole; and
    an anvil-roller side packing configured to seal between an outer peripheral surface of the tip of the anvil-roller side refrigerant introducing pipe and the inner peripheral surface of the anvil-roller side center hole, wherein
    the anvil-roller side refrigerant flowing part includes an entrance for introducing the refrigerant into the anvil-roller side refrigerant flowing part from outside and an exit for discharging the refrigerant to the outside of the anvil-roller side refrigerant flowing part;
    the entrance of the anvil-roller side refrigerant flowing part communicates with the anvil-roller side center hole at a position closer to the tip of the anvil-roller side refrigerant introducing pipe than the anvil-roller side packing and the exit of the anvil-roller side refrigerant flowing part communicates with the anvil-roller side center hole at a position closer to a base end of the anvil-roller side refrigerant introducing pipe than the anvil-roller side packing; and
    the anvil-roller side refrigerant flowing part includes parts extending in a radial direction of the anvil roller from the entrance and the exit thereof toward an outer peripheral surface of the anvil roller.

4. A composite sheet manufacturing device for compounding strips produced from a first sheet and a second sheet, the first sheet having an adhesive surface, the device comprising:
    a cutter roller configured to rotate about a predetermined axis and including a cutter;

an anvil roller configured to cut the first sheet into strips by introducing the first sheet to between the cutter roller and the anvil roller by rotating relative to the cutter roller; and
a cooling unit configured to cool at least one of the cutter of the cutter roller and the anvil roller by a refrigerant;
a press roller configured to press the strips adhered onto the second sheet against the outer peripheral surface of the anvil roller via the second sheet; and
a pressing pressure adjustment mechanism capable of adjusting a pressing pressure of the press roller against the anvil roller; wherein the pressing pressure adjustment mechanism includes:
a bracket configured to support the press roller rotatably about a center axis of the press roller;
a supporting portion configured to support the bracket swingably about an axis parallel to a center axis of the press roller; and
a stopper capable of regulating a swinging movement of the bracket with the bracket swung to a predetermined regulating position and changing the regulating position
a pressing member configured to press the bracket in a direction to swing the bracket toward the regulating position and to support the bracket so that a position of the press roller is changed automatically to a proper position corresponding to the thickness of the strip and the second sheet.

\* \* \* \* \*